(12) United States Patent
Hegde et al.

(10) Patent No.: US 11,532,390 B2
(45) Date of Patent: Dec. 20, 2022

(54) METHOD AND SYSTEM FOR VALIDATING PARAMETERS IN A MEDICAL STUDY

(71) Applicant: Siemens Healthcare GmbH, Erlangen (DE)

(72) Inventors: Ananda Hegde, Bangalore (IN); Reena Paliwal, Karnataka (IN)

(73) Assignee: Siemens Healthcare GmbH, Erlangen (DE)

( * ) Notice: Subject to any disclaimer, the term of this patent is extended or adjusted under 35 U.S.C. 154(b) by 221 days.

(21) Appl. No.: 16/227,966

(22) Filed: Dec. 20, 2018

(65) Prior Publication Data

US 2019/0198159 A1  Jun. 27, 2019

(30) Foreign Application Priority Data

Dec. 21, 2017  (EP) .................................... 17209615

(51) Int. Cl.
*G16H 30/40* (2018.01)
*G16H 40/20* (2018.01)
(Continued)

(52) U.S. Cl.
CPC .......... *G16H 30/40* (2018.01); *A61B 6/5217* (2013.01); *A61B 6/5294* (2013.01); *G16H 30/00* (2018.01);
(Continued)

(58) Field of Classification Search
None
See application file for complete search history.

(56) References Cited

U.S. PATENT DOCUMENTS

| 9,129,044 B2 | 9/2015 | Shih et al. |
| 2003/0074228 A1 | 4/2003 | Walsh |

(Continued)

FOREIGN PATENT DOCUMENTS

| WO | WO2013049818 A1 | 4/2013 | |
| WO | WO-2014115735 A1 * | 7/2014 | ............... A61B 6/03 |

OTHER PUBLICATIONS

Gunter, J.L., Bernstein, M.A., Borowski, B.J., Ward, C.P., Britson, P.J., Felmlee, J.P., Schuff, N., Weiner, M. and Jack, C.R. (2009), Measurement of MRI scanner performance with the ADNI phantom. Med. Phys., 36: 2193-2205. https://doi.org/10.1118/1.3116776 (Year: 2099).*

(Continued)

*Primary Examiner* — Rachelle L Reichert
(74) *Attorney, Agent, or Firm* — Lempia Summerfield Katz LLC

(57) ABSTRACT

A method and system for validating a parameter in a medical study are disclosed. The method includes receiving the medical study from a source. A processor determines a first parameter of the medical study to be validated. An imaging protocol is received from a configuration file in an imaging unit. The imaging protocol includes a second parameter corresponding to the first parameter in the medical study. The processor determines if there is a mismatch of the first parameter in the medical study and the second parameter in the imaging protocol. If there is a mismatch, the processor corrects the first parameter in the medical study based on the second parameter in the imaging protocol to validate the medical study.

19 Claims, 10 Drawing Sheets

(51) Int. Cl.
*G16H 30/20* (2018.01)
*A61B 6/00* (2006.01)
*G16H 30/00* (2018.01)
*G16H 40/63* (2018.01)
*A61B 6/03* (2006.01)

(52) U.S. Cl.
CPC ............. *G16H 30/20* (2018.01); *G16H 40/20* (2018.01); *G16H 40/63* (2018.01); *A61B 6/032* (2013.01); *A61B 6/544* (2013.01)

(56) References Cited

U.S. PATENT DOCUMENTS

| | | | |
|---|---|---|---|
| 2008/0103834 A1* | 5/2008 | Reiner | A61B 6/5294 705/3 |
| 2010/0114597 A1 | 5/2010 | Shreiber et al. | |
| 2012/0148131 A1* | 6/2012 | Couch | G06T 7/337 382/131 |
| 2012/0148132 A1* | 6/2012 | Couch | G01T 1/02 382/131 |
| 2012/0213326 A1* | 8/2012 | Walker | G06F 19/00 378/4 |
| 2014/0278448 A1 | 9/2014 | Sadeghi et al. | |

OTHER PUBLICATIONS

European Office Action for European Application No. 17209615. 8-1126 dated Jun. 29, 2020.
Abul-Kasim, Kasim, et al. "Radiation dose optimization in CT planning of corrective scoliosis surgery: a phantom study." The Neuroradiology Journal 21.3 (2008): 374-382.
Li, Xiang, et al. "Patient-specific radiation dose and cancer risk for pediatric chest CT." Radiology 259.3 (2011): 862-874.

\* cited by examiner

Study Id:
Time:                                    Oct 09, 2015,    09:52:50
Acc. Number:
Total DLP:                          1427.7 mGy*cm
Est.         savings:                  43.28%

| # | Description | Mode | CTDI (mGy) | DLP (mGy*cm) |
|---|---|---|---|---|
| 1 |  | Surview | 0.0 | 0.00 |
| 2 | ABD PEL WITH | Helical | 14.6 | 727.13 |

FIG 7

Time: Mar 23, 2015, 09:33:58
Total DLP: 588.8 mGy*cm

| Dose # | Description | Scan Mode | mAs | kv | CTDIvol (mGy) | DLP (mGy*cm) | Phantom Type (cm) |
|---|---|---|---|---|---|---|---|
| 1 | TOPOGRAM | Surview | 1 | 120 | 0.10 | 7.0 | 16 cm |
| 2 | Locator | Stationary | N/A | 100 | 1.68 | 1.7 | 32 cm |
| 2 | Locator | Stationary | N/A | 100 | 1.68 | 1.7 | 32 cm |
| 2 | Tracker | Stationary | N/A | 100 | 11.74 | 11.7 | 32 cm |
| 2 | TAVI AORTA 0.8MM | Axial | N/A | 100 | 10.30 | 566.6 | 32 cm |

700

METHOD AND SYSTEM FOR VALIDATING PARAMETERS IN A MEDICAL STUDY

PRIORITY

This application claims the benefit of EP 17209615.8, filed on Dec. 21, 2017, which is hereby incorporated by reference in its entirety.

FIELD OF TECHNOLOGY

The present embodiments relate to validating parameters in a medical study.

BACKGROUND

A digital imaging and communications in medicine (DICOM) file is generated when a patient undergoes an imaging/examination procedure, such as, for example, a computed tomography (CT) scan. The DICOM file contains a number of attributes, including patient name and identification details, age, details of the examination procedure, and image pixel data. The DICOM file also includes dose values pertaining to the imaging procedure and one or more tags associated with each attribute in the DICOM file. An imaging protocol pertaining to the imaging procedure is defined by an operator, corresponding to which attribute data is captured onto the DICOM file. As the imaging protocol is defined by the operator manually, the scope of error in inputting the attributes is high. Therefore, in an event where an attribute is captured incorrectly in the DICOM file, the DICOM file may be invalidated due to erroneous values. For example, if dose values are captured incorrectly in the DICOM file, a physician examining the medical study may provide wrong medical analysis to the patient. Incorrect dose values may further impact all the medical applications that make use of the DICOM file for processing.

SUMMARY AND DESCRIPTION

The scope of the present invention is defined solely by the appended claims and is not affected to any degree by the statements within this summary.

There exists a need to provide a method and a system that validates the parameters in a medical study by identifying and correcting the mismatches found between parameters in an imaging protocol and a medical study.

The present embodiments may obviate one or more of the drawbacks or limitations in the related art. For example, a method and a system to validate the parameters in a medical study, thereby rendering an accurate and valid medical study for medical use, are provided.

A method of validating parameters in a medical study, a local transmission unit, a system, a computer program product, and a computer-readable medium that correct a first parameter in the medical study based on a second parameter in an imaging protocol to validate the medical study are provided.

In the following, the present embodiments are described with respect to the local transmission unit as well as with respect to the method. Features, advantages, or alternative embodiments herein may be assigned to the other objects, and vice versa. In other words, the local transmission unit may be improved with features described in the context of the method. In this case, the functional features of the method are embodied by objective units of the local transmission unit.

The present embodiments achieve correct, if there is a mismatch, the parameter in the medical study based on the parameter in the imaging protocol to validate the medical study. An advantage is that as the mismatch between values in the imaging protocol and the medical study is corrected, a valid DICOM file is generated. Therefore, such valid DICOM file may be used for accurate further medical analysis. Correct examination of a patient's medical condition is provided using a valid DICOM file/medical study.

The present embodiments describe a method of validating a parameter in a medical study. The method includes receiving, by an interface, the medical study from a source. The source may be, for example, a medical database. The medical database may contain medical data obtained from, but not limited to, equipment (e.g., scanners; hospitals; medical professionals; and other providers that may be involved in patient care). In an embodiment, the medical database may be present in cloud. The interface may be, for example, a data bus that is configured to receive data from the medical database. Alternatively, the interface may be an adapter module coupled to the medical scanner. The adapter module creates an interface between the scanner and the cloud component. The adapter module may be configured to fetch medical study (e.g., digital imaging and communications in medicine (DICOM) study) from the scanner. Such DICOM study may include medical parameters such as, for example, dose values, DICOM tag information, etc. A first parameter to be validated from the medical study is determined by a processing unit. One of the parameters in the medical study may be captured incorrectly. Because of this, the medical study may be rendered invalid for further analysis. Therefore, determination of a parameter to be validated in the medical study is to be provided. The interface is further configured to receive an imaging protocol from a configuration file in an imaging unit. An imaging protocol may contain one or more parameters pertaining to image acquisition by the medical scanner. Therefore, the imaging protocol includes parameters that may correspond to the parameters in the medical study. A second parameter in the imaging protocol that corresponds to the first parameter in the medical study is identified. The corresponding second parameter to the first parameter may be identified, for example, using DICOM tag value. The corresponding second parameter in the imaging protocol allows identification of an erroneous recording of the first parameter in the medical study. The method further includes determining, by the processing unit, if there is a mismatch of the first parameter in the medical study and the second parameter in the imaging protocol. If there is a mismatch, the first parameter in the medical study is corrected based on the second parameter in the imaging protocol to validate the medical study. The advantage of the present embodiments is that the accuracy of the parameters in the medical study is maintained. Therefore, generation of erroneous medical studies is reduced, thereby enabling accurate processing of medical data.

According to an embodiment, the medical study is a digital imaging and communications in medicine (DICOM) study.

According to another embodiment, in determining a mismatch of the first parameter and the second parameter, the method further includes comparing, by the processing unit, the first parameter in the medical study with the corresponding second parameter in the imaging protocol. An estimate of similarity between the first parameter and the second parameter is performed to identify a mismatch in the parameters. For example, if the first parameter is a DICOM tag, the tag value of the DICOM tag is mapped to the tag value of the second parameter in the imaging protocol to identify discrepancy. The comparison of the first parameter and the second parameter may be performed, for example, to identify: difference in the value associated with the first parameter and the second parameter; if the value associated with the second parameter has been input in the imaging protocol; or if the value of the value associated with the first parameter has been input in the medical study. Comparing the first parameter and the second parameter may also be understood as analysis of values associated with the first parameter and the second parameter to determine a matching index. A high matching index indicates that the first parameter and the second parameter match. A low matching index may indicate a mismatch between the first parameter and the second parameter. The advantage of comparing the first parameter and the second parameter is the identification of mismatch between the values associated with the first parameter and the second parameter. Therefore, the inconsistency in the data included in the medical study and the imaging protocol is determined. Based on this determination, the validation of the medical study may be initiated.

According to a further embodiment, in correcting the first parameter in the medical study, the method includes determining, by the processing unit, an age of a patient being examined and/or a phantom size based on the age of the patient. The age of the patient being examined may be present in the medical study and/or the imaging protocol. Alternatively, the medical study and/or the imaging protocol may contain a date of birth of the patient being examined. Therefore, the age of the patient may be determined from the date of birth indicated in the medical study and/or the imaging protocol. A phantom is an object that is used to evaluate the performance of an imaging device/medical scanner. The phantom responds to the imaging process in a similar manner to that of a tissue or organ of an organism to be imaged. The size of the phantom is determined based on the age of the patient. The advantage of determination of the age of the patient and/or the size of the phantom is that the dosage of radiation to be given to the patient is ascertained accurately. Therefore, dosage values are recorded accurately in the medical study.

According to a further embodiment, in correcting the first parameter in the medical study, the method further includes normalizing by the processing unit the phantom size in the imaging protocol based on the age of the patient and correcting, by the processing unit, the first parameter in the medical study based on the normalized phantom size in the imaging protocol. In an embodiment, the phantom size determined according to the age of the patient may not be correctly recorded in the imaging protocol. Therefore, the dose value of radiation may be captured incorrectly. Thus, the phantom size input in the imaging protocol is normalized to the phantom size determined based on the age of the patient. By normalizing the phantom size, it is provided that the phantom size is uniformly and accurately recorded in the imaging protocol. 'Normalization' may also be, for example, 'standardization', where the phantom size value is made consistent throughout the imaging protocol. In an embodiment, an alert or notification may be generated in case of a mismatch to notify a user operating the medical scanner of the mismatch. The alert or notification may appear on a display unit of the medical scanner or the computing unit of the user as a pop-up window. The notification apart with the details of the mismatch may include, for example, an option to normalize the phantom size based on the determined age of the patient. The option may be chosen by the user to perform normalization of the phantom size values and correction of the first parameter in the medical study. The user may, through the graphical user interface of the display unit, choose to perform the normalization of the phantom size value, thereby correcting the first parameter in the medical study. Once the phantom size value is normalized in the imaging protocol, the first parameter in the medical study is corrected according to the normalized values. The first parameter may be a value that is dependent on the phantom size value. Such parameter may be, for example, dose values. The dose value changes according to the size of the phantom used for medical imaging. Size-specific dose estimation may be performed to ascertain the dose values corresponding to the determined phantom size. The estimation of dose value based on phantom size may be made according to procedures that may be well known to a person skilled in the art. Advantageously, correction of the first parameter in the medical study in accordance with the imaging protocol enables accurate recordation of parameters in the medical study. Therefore, efficient analysis of the medical study is enabled so as to provide unambiguous treatment to the patient.

According to an embodiment, in correcting the first parameter in the medical study, the method includes comparing, by the processing unit, a second parameter in the imaging protocol with the first parameter in the medical study. An estimate of similarity between the first parameter and the second parameter is performed to identify a mismatch in the parameters. If there is a mismatch, a dose index value and scan length value in the imaging protocol is determined by the processing unit. A dose index value specifies the radiation intensity required to perform the medical examination. Scan length is the length of the area on the patient being scanned. A product of the dose index value and the scan length value is calculated to determine a dose length product (DLP) value. A dose length product indicates the amount of radiation required to perform a medical examination (e.g., a computed tomography examination) and is quantified in a phantom of a defined size. On determination of the DLP value, the first parameter in the medical study is corrected by the processing unit based on the determined second parameter. Correcting the first parameter in the medical study may also be understood as inputting or recording the determined second parameter into the medical study. Correcting may also refer to replacing the existing first parameter value in the medical study with the determined second parameter. Advantageously, the second parameter is determined accurately in this act, thereby eliminating the risk of capturing incorrect values in the imaging protocol and/or in the medical study. Therefore, this enables generation of a valid medical study for further use.

According to an embodiment, the first parameter is the DLP value in the medical study, and the second parameter is DLP value in the imaging protocol.

According to another embodiment, the first parameter in the medical study includes dose values accumulated after an irradiation event of medical imaging. Following an irradiation event of medical imaging, the dose values are recorded in the medical study. These dose values, in an embodiment, may be the first parameter to be validated according to the method.

According to yet another embodiment, the first parameter of the medical study includes a DICOM tag. A DICOM tag enables identification of an attribute in a medical study.

According to another embodiment, the second parameter in the imaging protocol includes dose values defined for the irradiation event of medical imaging. The imaging protocol includes values defined for an irradiation event. Based on the values input in the imaging protocol, the patient being examined is irradiated to obtain a medical image. The dose values in the imaging protocol may be used to validate the dose values in the medical study. Advantageously, this enables accurate recording of medical parameters in the medical study, thereby generating a valid medical study.

One or more of the present embodiments also relate to a local transmission unit configured for validating a parameter in a medical study. The local transmission unit includes an interface configured to receive the medical study from a source. The source may be, for example, a medical database. The medical database may contain medical data obtained from, but not limited to, medical equipment (e.g., scanners; hospitals; medical professionals; and other providers that may be involved in patient care). In an embodiment, the medical database may be present in cloud. The interface may be, for example, a data bus that is configured to receive data from the medical database. Alternatively, the interface may be an adapter module coupled to the medical scanner. The adapter module creates an interface between the scanner and the cloud component. The adapter module may be configured to fetch medical study (e.g., digital imaging and communications in medicine (DICOM) study) from the scanner. Such DICOM study may include medical parameters such as, for example, dose values, DICOM tag information, etc. The interface is further configured to receive an imaging protocol from a configuration file in an imaging unit. An imaging protocol may contain one or more parameters pertaining to image acquisition by the medical scanner. Therefore, the imaging protocol includes parameters that may correspond to the parameters in the medical study. A second parameter in the imaging protocol that corresponds to the first parameter in the medical study is identified. The corresponding second parameter to the first parameter may be identified, for example, using DICOM tag value. The corresponding second parameter in the imaging protocol allows identification of an erroneous recording of the first parameter in the medical study.

The local transmission unit further includes a processing unit configured to determine a first parameter to be validated from the medical study. One of the parameters in the medical study may be captured incorrectly. Because of this, the medical study may be rendered invalid for further analysis. Therefore, determination of a parameter to be validated in the medical study is to be provided. The processing unit is further configured to determine, by the processing unit, if there is a mismatch of the first parameter in the medical study and the second parameter in the imaging protocol. If there is a mismatch, the processing unit is configured to correct the first parameter in the medical study based on the second parameter in the imaging protocol to validate the medical study. The advantage of one or more of the present embodiments is that the accuracy of the parameters in the medical study is maintained. Therefore, generation of erroneous medical studies is reduced, thereby enabling accurate processing of medical data. The local transmission unit is configured to execute a method.

According to an embodiment, the medical study is a digital imaging and communications in medicine (DICOM) study.

According to another embodiment, in determining a mismatch of the first parameter and the second parameter, the processing unit is further configured to compare the first parameter in the medical study with the corresponding second parameter in the imaging protocol. An estimate of similarity between the first parameter and the second parameter is performed to identify a mismatch in the parameters. For example, if the first parameter is a DICOM tag, the tag value of the DICOM tag is mapped to the tag value of the second parameter in the imaging protocol to identify discrepancy. The comparison of the first parameter and the second parameter may be performed, for example, to identify: difference in the value associated with the first parameter and the second parameter; if the value associated with the second parameter has been input in the imaging protocol; or if the value of the value associated with the first parameter has been input in the medical study. Comparing the first parameter and the second parameter may also be understood as analysis of values associated with the first parameter and the second parameter to determine a matching index. A high matching index indicates that the first parameter and the second parameter match. A low matching index may indicate a mismatch between the first parameter and the second parameter. The advantage of comparing the first parameter and the second parameter is the identification of mismatch between the values associated with the first parameter and the second parameter. Therefore, the inconsistency in the data included in the medical study and the imaging protocol is determined based on which the validation of the medical study may be initiated.

According to a further embodiment, in correcting the first parameter in the medical study, the local transmission unit is further configured to determine, by the processing unit, an age of a patient being examined and/or a phantom size based on the age of the patient. The age of the patient being examined may be present in the medical study and/or the imaging protocol. Alternatively, the medical study and/or the imaging protocol may contain a date of birth of the patient being examined. Therefore, the age of the patient may be determined from the date of birth indicated in the medical study and/or the imaging protocol. A phantom is an object that is used to evaluate the performance of an imaging device/medical scanner. The phantom responds to the imaging process in a similar manner to that of a tissue or organ of an organism to be imaged. The size of the phantom is determined based on the age of the patient. The advantage of determination of the age of the patient and/or the size of the phantom is that the dosage of radiation to be given to the patient is ascertained accurately. Therefore, dosage values are recorded accurately in the medical study.

According to a further embodiment, in correcting the first parameter in the medical study, the local transmission unit is further configured to normalize the phantom size in the imaging protocol based on the age of the patient and correcting by the processing unit the first parameter in the medical study based on the normalized phantom size in the imaging protocol. In an embodiment, the phantom size determined according to the age of the patient may not be correctly recorded in the imaging protocol. Therefore, the dose value of radiation may be captured incorrectly. Thus, the phantom size input in the imaging protocol is normalized to the phantom size determined based on the age of the patient. By normalizing the phantom size, it is provided that the phantom size is uniformly and accurately recorded in the imaging protocol. 'Normalization' may also be understood as, for example, 'standardization', where the phantom size value is made consistent throughout the imaging protocol. In an embodiment, the local transmission unit may further be configured to generate an alert or notification in case of a mismatch, to notify a user operating the medical scanner of the mismatch. The alert or notification may appear on a display unit of the medical scanner or the computing unit of the user as a pop-up window. The notification apart with the details of the mismatch may include, for example, an option to normalize the phantom size based on the determined age of the patient. The option may be chosen by the user to perform normalization of the phantom size values and correction of the first parameter in the medical study. The user may, through the graphical user interface of the display unit, choose to perform the normalization of the phantom size value, thereby correcting the first parameter in the medical study. Once the phantom size value is normalized in the imaging protocol, the first parameter in the medical study is corrected according to the normalized values. The first parameter may be a value that is dependent on the phantom size value. Such parameter may be, for example, dose values. The dose value changes according to the size of the phantom used for medical imaging. Size-specific dose estimation may be performed to ascertain the dose values corresponding to the determined phantom size. The estimation of dose value based on phantom size may be made according to procedures that may be well known to a person skilled in the art. Advantageously, correction of the first parameter in the medical study in accordance with the imaging protocol enables accurate recordation of parameters in the medical study. Therefore, efficient analysis of the medical study is enabled so as to provide unambiguous treatment to the patient.

According to an embodiment, in correcting the first parameter in the medical study, the local transmission unit is configured to compare a second parameter in the imaging protocol with the first parameter in the medical study. An estimate of similarity between the first parameter and the second parameter is performed to identify a mismatch in the parameters. If there is a mismatch, a dose index value and scan length value in the imaging protocol is determined by the processing unit. A dose index value specifies the radiation intensity required to perform the medical examination. Scan length is the length of the area on the patient being scanned. A product of the dose index value and the scan length value is calculated to determine a dose length product (DLP) value. A dose length product indicates the amount of radiation required to perform a medical examination (e.g., a computed tomography examination) and is quantified in a phantom of a defined size. On determination of the DLP value, the first parameter in the medical study is corrected by the processing unit based on the determined second parameter. Correcting the first parameter in the medical study may also be understood as inputting or recording the determined second parameter into the medical study. Correcting may also refer to replacing the existing first parameter value in the medical study with the determined second parameter. Advantageously, the second parameter is determined accurately in this act, thereby eliminating the risk of capturing incorrect values in the imaging protocol and/or in the medical study. Therefore, this enables generation of a valid medical study for further use.

According to an embodiment, the first parameter is the DLP value in the medical study, and the second parameter is DLP value in the imaging protocol.

According to another embodiment, the first parameter in the medical study includes dose values accumulated after an irradiation event of medical imaging. Following an irradiation event of medical imaging, the dose values are recorded in the medical study. These dose values, in an embodiment, may be the first parameter to be validated according to the method.

According to yet another embodiment, the first parameter of the medical study includes a DICOM tag. A DICOM tag enables identification of an attribute in a medical study.

According to another embodiment, the second parameter in the imaging protocol includes dose values defined for the irradiation event of medical imaging. The imaging protocol includes values defined for an irradiation event. Based on the values input in the imaging protocol, the patient being examined is irradiated to obtain a medical image. The dose values in the imaging protocol may be used to validate the dose values in the medical study. Advantageously, this enables accurate recording of medical parameters in the medical study, thereby generating a valid medical study.

One or more of the present embodiments also relate to a system for validating a parameter is a medical study. The system includes a medical scanner configured to scan an object and generate a medical study. The medical study includes a first parameter to be validated. The object may be, for example, a patient to be examined. The medical scanner may be, for example, but not limited to a computed tomography scanner, an X-ray unit, or a magnetic resonance imaging unit. The system further includes a local transmission unit including an interface that may be configured to receive the medical study from the medical scanner. The interface may be, for example, a cloud adapter module that may be configured to receive medical images from the medical scanner and transfer the medical images to the cloud computing environment. The local processing unit further includes a processing unit in a cloud computing environment. The processing unit is configured to validate a parameter in the medical study. The processing unit in the cloud environment may be coupled to a database, such as a blob storage, which may contain all the medical images received from the medical scanner. The advantage of one or more of the present embodiments is that the validation of the parameter in the medical study may be performed in a cloud environment. This enables access to the processing unit for validation of the medical study to different users.

In one aspect, a computer program product includes a computer program. The computer program is loadable into a storage unit of a local transmission unit. The computer program includes program code sections to make the local transmission unit execute a method according to an aspect when the computer program is executed in the local transmission unit.

In one aspect, a computer-readable medium, on which program code sections of a computer program are saved, is provided. The program code sections are loadable into and/or executable in a local transmission unit to make the local transmission unit execute the method according to an aspect when the program code sections are executed in the local transmission unit.

The realization of one or more of the present embodiments by a computer program product and/or a computer-readable medium has the advantage that already existing allocation systems may be easily adopted by software updates in order to work as proposed.

The computer program product may be, for example, a computer program or may include another element apart from the computer program. This other element may be hardware (e.g., a memory device), on which the computer program is stored, a hardware key for using the computer program and the like, and/or software (e.g., a documentation or a software key for using the computer program).

The computer program product may be, for example, a computer program or may include another element apart from the computer program. This other element may be hardware (e.g., a memory device), on which the computer program is stored, a hardware key for using the computer program and the like, and/or software (e.g., a documentation or a software key for using the computer program).

BRIEF DESCRIPTION OF THE DRAWINGS

FIG. 6 illustrates an embodiment of a medical study containing dose length product value.

FIG. 7 illustrates an embodiment of a medical study depicting phantom size values.

DETAILED DESCRIPTION

Figure 1:
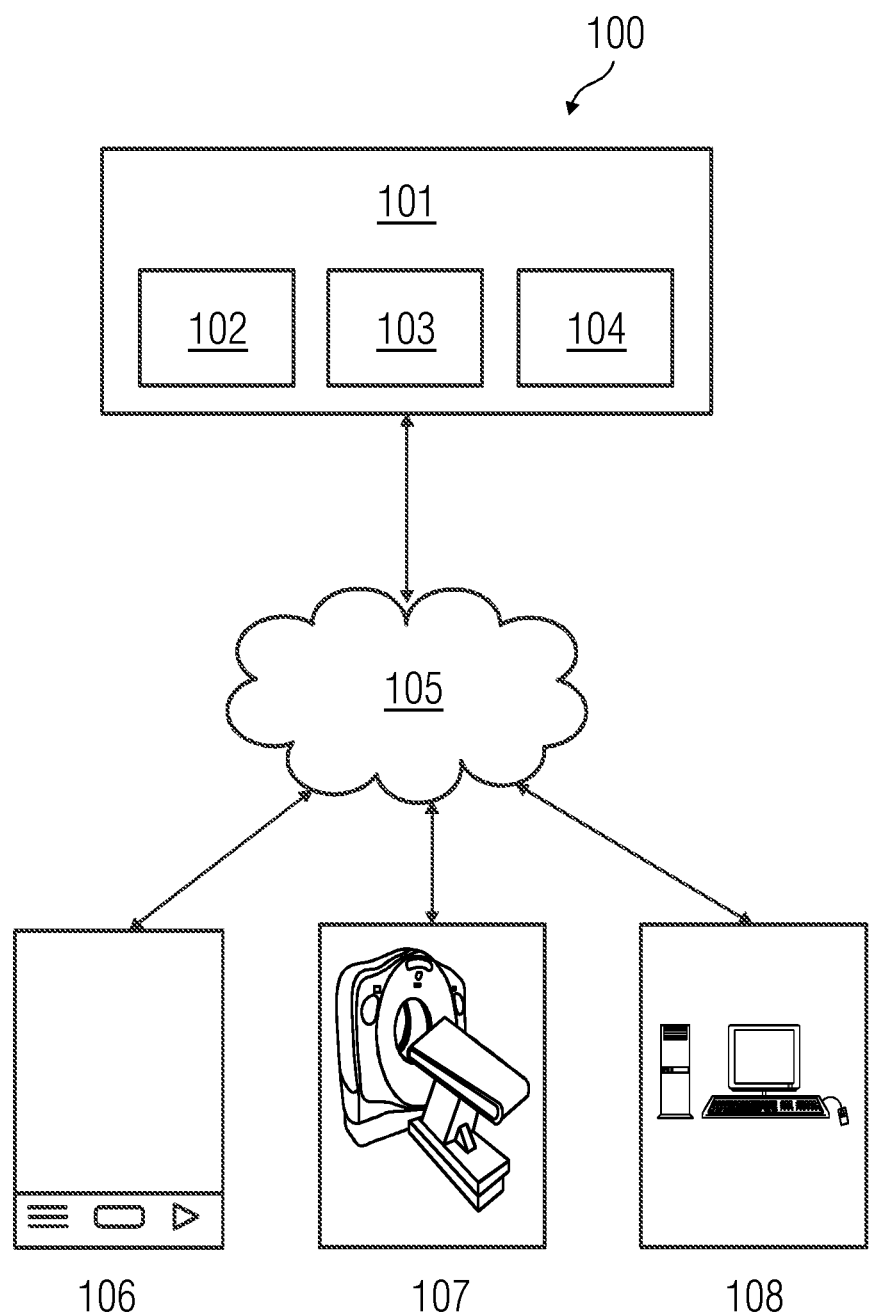
FIG. 1 illustrates a block diagram of a client-server architecture that provides geometric modeling of components representing different parts of a real world object, according to an embodiment.

Embodiments are described in detail below. The various embodiments are described with reference to the drawings, where like reference numerals are used to refer to like elements throughout. In the following description, for purpose of explanation, numerous specific details are set forth in order to provide a thorough understanding of one or more embodiments. Such embodiments may be practiced without these specific details.

FIG. 1 provides an illustration of a block diagram of a client-server architecture that is a geometric modeling of components representing different parts of real-world objects, according to an embodiment. The client-server architecture 100 includes a server 101, a mobile device 106, a computing unit 108, and a medical scanner 107. The mobile device 106, the computing unit 108, and the medical scanner 107 are connected to the server 101 via a network 105 (e.g., local area network (LAN)), wide area network (WAN), WiFi, etc. In one embodiment, the server 101 is deployed in a cloud computing environment. As used herein, "cloud computing environment" refers to a processing environment including configurable computing physical and logical resources such as, for example, networks, servers, storage, applications, services, etc., and data distributed over the network 105 (e.g., the Internet). The cloud computing environment provides on-demand network access to a shared pool of the configurable computing physical and logical resources. The server 101 may include blob storage or a medical database 102 that includes medical images obtained from the medical scanner 107. The medical database 102 may contain medical data obtained from, but not limited to, one or more medical equipment (e.g., scanners, hospitals, medical professionals) and other providers that may be involved in patient care. The medical database may obtain patient medical information from, for example, picture archiving and communication system (PACS), hospital information system (HIS), laboratory information system (LIS), and radiology information system (RIS). The server 101 may further include a validation module 103 that is configured to validate a parameter in a medical study. The server 101 may include an interface 104 that receives medical data (e.g., medical images from the medical scanner 107) and transfers the medical images to the medical database 102. Additionally, the interface 104 may also communicate with the mobile device 106 and the computing unit 108 via the network 105.

The mobile device 106 and/or the computing unit 108 are used by a user to access medical images to be validated. The medical images on the server 101 may be accessed by the user via a graphical user interface of an end user web application.

Figure 2:
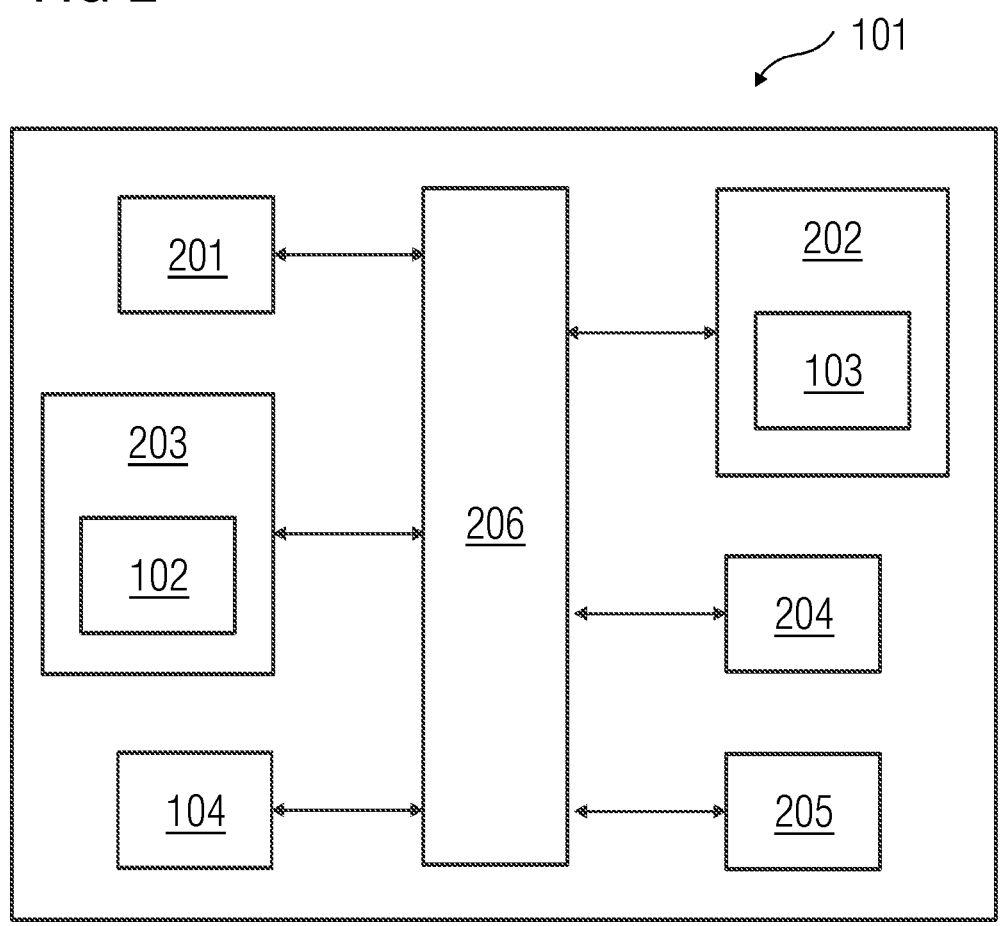
FIG. 2 illustrates a block diagram of a local transmission unit in which an embodiment of a method for validation of a parameter in a medical study may be implemented.

FIG. 2 is a block diagram of a local transmission unit 101 in which an embodiment may be implemented, for example, as a system to validate a parameter in a medical image, configured to perform the processes as described therein. The server 101 is an exemplary implementation of the local transmission unit in FIG. 1. In FIG. 2, the local transmission unit 101 includes a processing unit 201 (e.g., a processor), a memory 202, a storage unit 203, an input unit 204, an output unit 205, a network interface 104, and a standard interface or bus 206. The local transmission unit 101 may be a computer (e.g., a personal computer), a workstation, a virtual machine running on host hardware, a microcontroller, or an integrated circuit. As an alternative, the local transmission unit 101 may be a real or a virtual group of computers (e.g., a "cluster" or a "cloud", respectively).

The processing unit 201, as used herein, may be any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processing unit 201 may also include embedded controllers, such as generic or programmable logic devices or arrays, application specific integrated circuits, single-chip computers, and the like. In general, a processing unit 201 may include hardware elements and software elements. The processing unit 201 may be configured for multithreading (e.g., the processing unit 201 may host different calculation processes at the same time, executing either in parallel or switching between active and passive calculation processes).

The memory 202 may be volatile memory and non-volatile memory. The memory 202 may be coupled for communication with the processing unit 201. The processing unit 201 may execute instructions and/or code stored in the memory 202. A variety of computer-readable storage media may be stored in and accessed from the memory 202. The memory 202 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory 202 includes a validation module 103 stored in the form of machine-readable instructions on any of the above-mentioned storage media and may be in communication with and executed by processing unit 201. When executed by the processing unit 201, the validation module 103 causes the processing unit 201 to validate a parameter in a medical study. In an alternate embodiment, the memory may also include a notification module (not illustrated) that is configured to generate an alert or notification for a user operating the medical scanner in case of a mismatch identified in the parameter in the medical study and a parameter in a imaging protocol. Method acts executed by the processing unit 201 to achieve the abovementioned functionality are elaborated upon in detail in FIGS. 3, 4, 5, 8, and 9.

The storage unit 203 may be a non-transitory storage medium that stores a medical database 102. The medical database 102 is a repository of medical information related to one or more patients that is maintained by a healthcare service provider. The input unit 204 may include an input such as keypad, touch-sensitive display, camera (e.g., a camera receiving gesture-based inputs), etc. capable of receiving input signal such as a medical data including patient information to be shared or allocated. The bus 206 acts as interconnect between the processing unit 201, the memory 202, the storage unit 203, the communication interface 104, the input unit 204, and the output unit 205.

The hardware depicted in FIG. 2 may vary for particular implementations. For example, other peripheral devices such as an optical disk drive and the like, Local Area Network (LAN)/Wide Area Network (WAN)/Wireless (e.g., Wi-Fi) adapter, graphics adapter, disk controller, input/output (I/O) adapter may also be used in addition or in place of the hardware depicted. The depicted example is provided for the purpose of explanation only and is not meant to imply architectural limitations with respect to the present disclosure.

A local transmission unit in accordance with an embodiment includes an operating system employing a graphical user interface. The operating system permits multiple display windows to be presented in the graphical user interface simultaneously with each display window providing an interface to a different application or to a different instance of the same application. A cursor in the graphical user interface may be manipulated by a user through the pointing device. The position of the cursor may be changed and/or an event such as clicking a mouse button may actuate a desired response.

One of various commercial operating systems, such as a version of Microsoft Windows™, a product of Microsoft Corporation located in Redmond, Wash. may be employed if suitably modified. The operating system is modified or created in accordance with the present disclosure, as described.

Disclosed embodiments provide systems and methods for analyzing medical data associated with a patient. For example, the systems and methods may perform validation of a parameter in a medical study.

Figure 3:
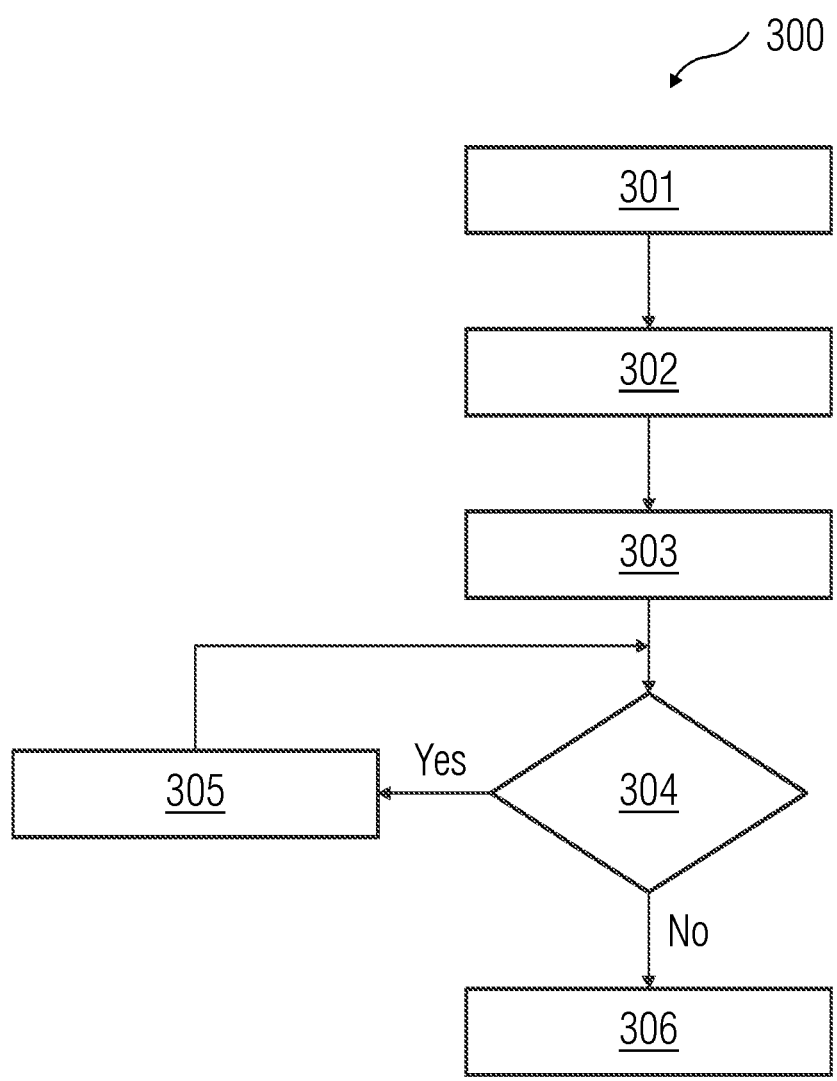
FIG. 3 illustrates a flow chart of an embodiment of a method of validating a parameter in a medical study.

FIG. 3 illustrates an embodiment of a method 300 of validating a parameter in a medical study. At act 301 of the method 300, the medical study and imaging protocol are obtained from the medical scanner via the interface 104. In an embodiment, the medical study is a Digital Imaging and Communications in Medicine (DICOM) study. The DICOM study includes medical data accumulated after an irradiation event of medical imaging. A DICOM study may include one or more parameters, for example, but not limited to, the date of birth of a patient being examined and/or the age, the gender of the patient, phantom size value, dose values of the radiation a patient is exposed to, and DICOM tags. An imaging protocol includes data defined for the irradiation event of medical imaging. At act 302, a first parameter to be validated in the medical study is determined by the processing unit 201. One of the parameters in the medical study may be captured incorrectly. Because of this, the medical study may be rendered invalid for further analysis. Therefore, determination of a parameter to be validated in the medical study is to be provided. In an embodiment, the first parameter is a dose value. Alternatively, the first parameter may be any parameter in the DICOM study that may require validation.

At act 303, a second parameter in the imaging protocol is determined by the processing unit 201. The second parameter in the imaging protocol is a parameter corresponding to the first parameter in the DICOM study. Therefore, if the first parameter is dose value, the second parameter determined from the imaging protocol is also dose value. The corresponding second parameter in the imaging protocol may be determined, for example, using DICOM tag values. At act 304, the first parameter and the second parameter are compared by the processing unit 201 to determine if there is a mismatch between the first parameter and the second parameter. An estimate of similarity between the first parameter and the second parameter is performed to identify a mismatch in the parameters. A high matching index indicates that the first parameter and the second parameter match. A low matching index may indicate a mismatch between the first parameter and the second parameter. The advantage of comparing the first parameter and the second parameter is the identification of mismatch between the values associated with the first parameter and the second parameter. Therefore, the inconsistency in the data included in the medical study and the imaging protocol is determined, based on which the validation of the medical study is initiated. If the values of the first parameter and the second parameter match, a structured report is generated by the processing unit 201 at act 306. A structured report encodes an imaging diagnostic report essential for Electronic Healthcare Record (EHR). If a mismatch between the first parameter and the second parameter is identified, the first parameter in the medical study is corrected based on the second parameter in the imaging protocol. A structured report is generated by the processing unit 201, at act 306, once the first parameter is corrected. This method enables correction of inconsistency in the data included in the medical study and the imaging protocol. Therefore, a valid medical study is generated for further analysis.

Figure 4:
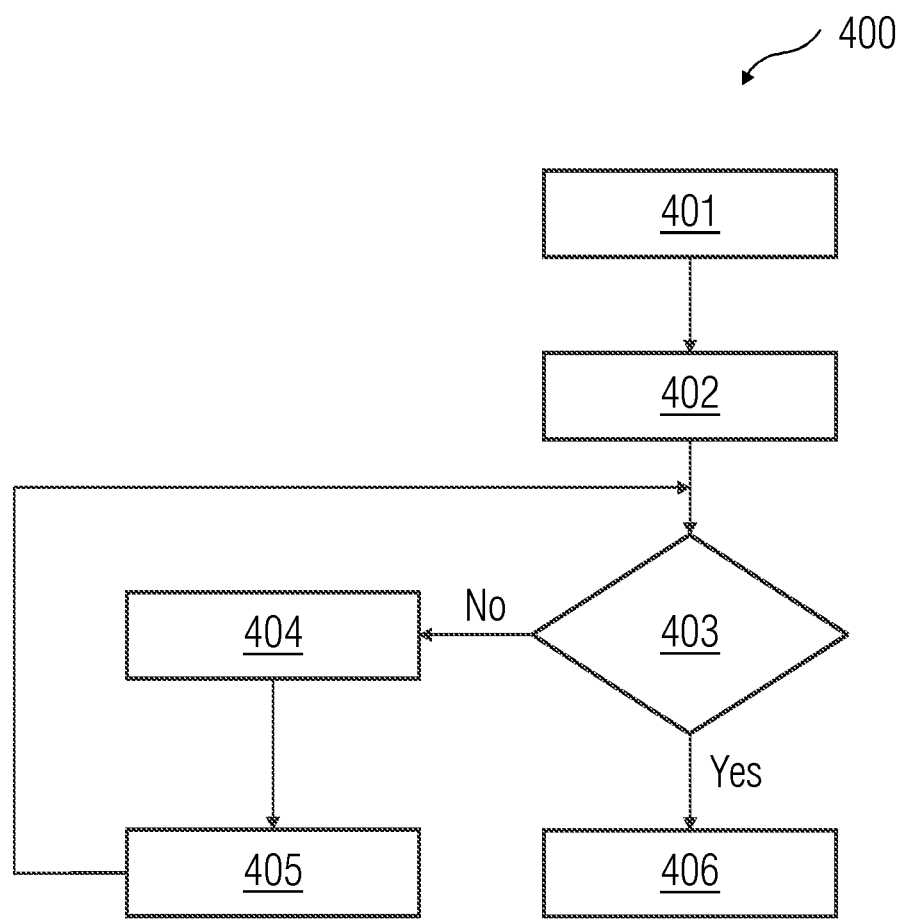
FIG. 4 illustrates a flowchart of an embodiment of a method of correcting a parameter in a medical study.

FIG. 4 illustrates a flowchart of an embodiment of a method 400 of correcting a parameter in a medical study. At act 401 of the method 400, the age of the patient being examined is determined by the processing unit 201. The age of the patient may be present in the DICOM study/imaging protocol. Alternatively, the DICOM study/imaging protocol may include a date of birth of the patient being examined. The age of the patient may therefore be determined from the date of birth in the DICOM study/imaging protocol. The age of the patient enables determination of the quantity of radiation that the patient may be exposed to. At act 402 of the method 400, a phantom size is determined by the processing unit 201 from the imaging protocol. A phantom or an imaging phantom is an object that is scanned or imaged before a patient is examined so as to determine the performance of the imaging device/medical scanner. The size of the phantom is proportional to the radiation dose value to which a patient being examined is to be exposed. Therefore, the size of the phantom enables identification of the radiation dose value. Therefore, with a change in the phantom size, the quantity of radiation may also be modified. At act 403 of the method 400, the phantom size recorded in the imaging protocol is mapped to the determined age of the patient. This enables the processing unit 201 determining if the size of the phantom is appropriate for the determined age of the patient. If the size of the phantom is not appropriate based on the age of the patient, at act 404, the phantom size is normalized in the imaging protocol based on the determined age of the patient. For example, based on the determined age, if the patient is an adult, the phantom size (diameter) would be 32 centimeter. FIG. 7 illustrates an embodiment of a medical study 700 including phantom sizes. As illustrated in FIG. 7, the phantom size may not be recorded correctly and therefore require normalization. At act 405 of the method 400, the first parameter in the DICOM study (e.g., the dose value is corrected based on the normalized phantom size). Therefore, the method acts enable correction of dose value in the DICOM study based on the normalized phantom size. Therefore, a valid DICOM study that may be used for accurate medical analysis of the patient is generated. At act 406 of the method 400, a structured medical report is generated after the dose values are corrected or if the phantom size corresponds to the patient age.

Figure 5:
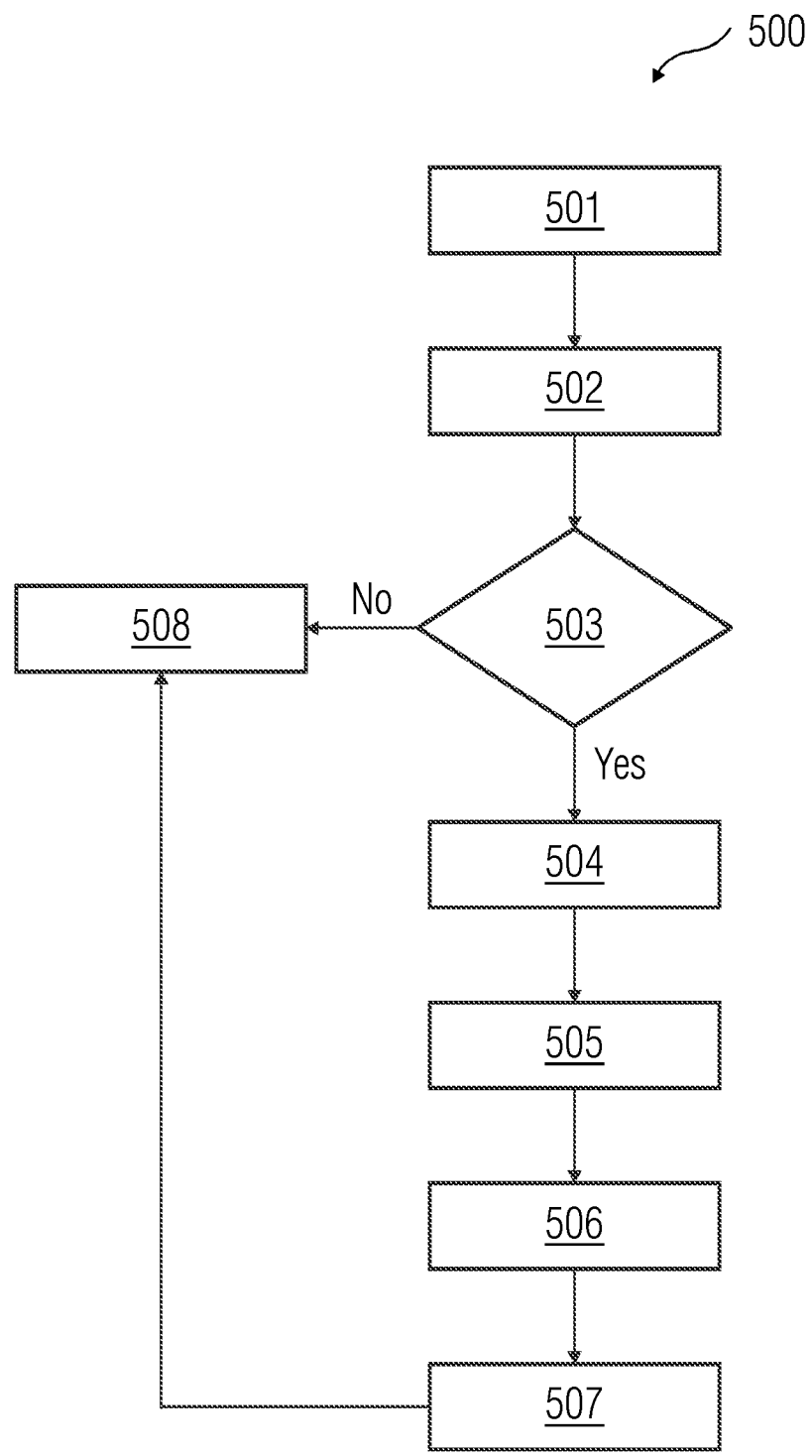
FIG. 5 illustrates a flowchart of another embodiment of a method of correcting a parameter in a medical study.

FIG. 5 illustrates a flowchart of yet another embodiment of a method 500 of correcting a parameter in a medical study. In an embodiment, the medical scanner 107 is a computed tomography scanner. At act 501 of the method 500, a first parameter in the medical study is determined by the processing unit 201. In an embodiment, the first parameter is a dose length product (DLP) value. A dose length product is the measure of total radiation that is to be provided to perform a computed tomography examination. The DLP value in the medical study may be recorded after the irradiation event. FIG. 6 illustrates an embodiment of a medical study 600 depicting dose length product value recorded. At act 502 of the method 500, a second parameter is identified from the imaging protocol by the processing unit 201. The second parameter corresponds to the first parameter determined from the medical study. Therefore, in the embodiment, the second parameter is the dose length product (DLP) value recorded in the imaging protocol. The DLP value in the imaging protocol may be defined before the irradiation event. The dose length product is a product of dose index or computed tomography dose index (CTDI) and the scan length. The dose index is the radiation intensity that is to be provided to perform a computed tomography examination. A scan length is the length of the area (e.g., in centimeter) on the patient being examined that may be irradiated for the medical examination. The first parameter and the second parameter are compared at act 503 of the method 500 to determine if there is a mismatch in the dose length product values in the medical study and the imaging protocol. If there is a mismatch, at act 504, a dose index value is determined. The dose index value may be recorded in the imaging protocol or may be obtained from the computed tomography scanner 107. At act 505, a scan length of the area being examined is determined by the processing unit to calculate a product of the dose index and the scan length. Therefore, the dose length product is determined. The dose length product in the medical study is corrected based on the determined dose length product value at act 507.

Figure 8:
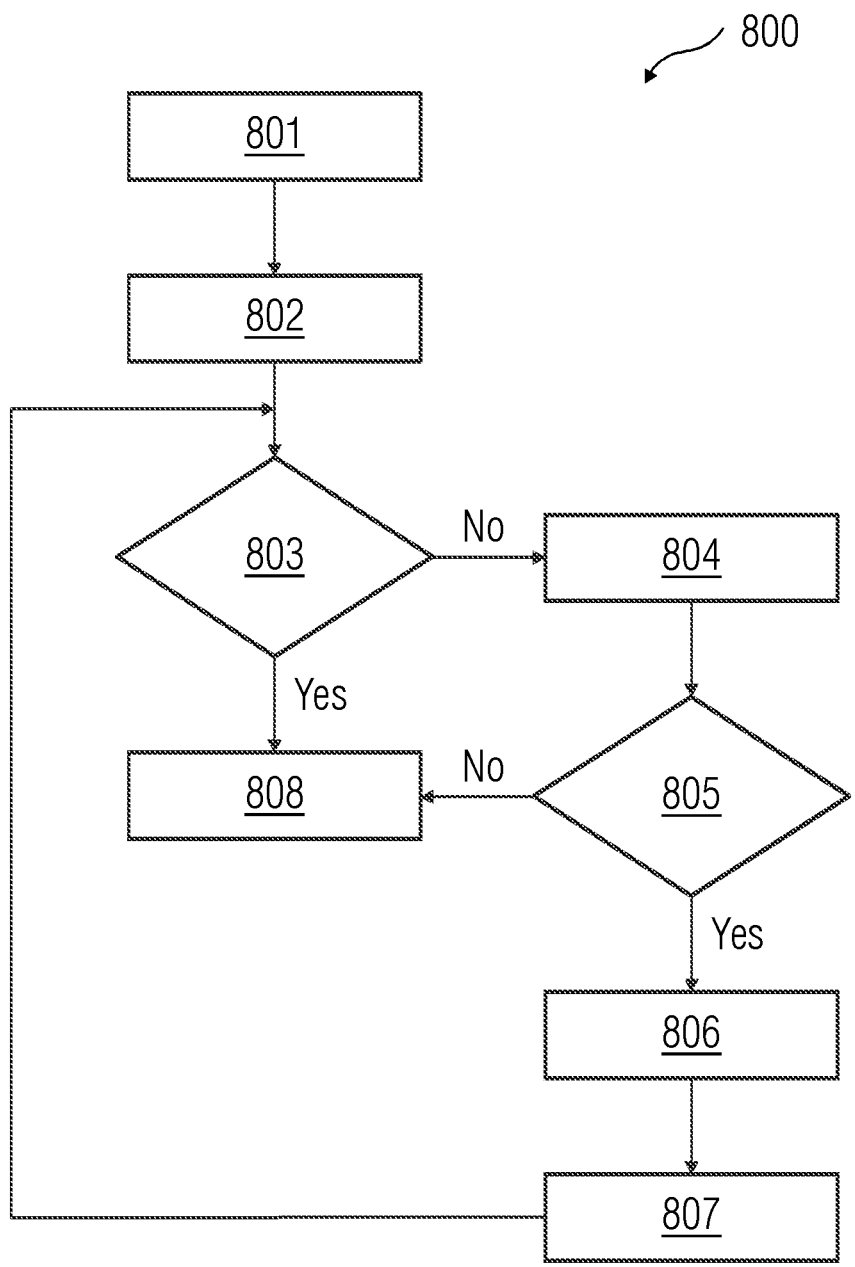
FIG. 8 illustrates a flowchart of another embodiment of a method of correcting a parameter in a medical study.

FIG. 8 illustrates a flowchart of yet another embodiment of a method 800 of correcting a parameter in a medical study. At act 801 of the method 800, the age of the patient being examined is determined by the processing unit 201. The age of the patient may also be determined from the date of birth of the patient in the imaging protocol/medical study. At act 802 of the method 800, the recorded phantom size is determined by the processing unit 201. At act 803, the age of the patient and the recorded are compared to identify if the values match. If the values do not match, at act 804, a notification or alert is generated for a user who may be operating the medical scanner 107 on the mobile device 106 or the computing unit 108. In an embodiment, the notification or alert appears as a pop-up window on the display unit. The computing unit 108 or the mobile device 106 of the user may also be configured to generate a sound alert when the notification is received on the mobile device 106 or the computing unit 108. The notification or alert enables the user to choose an option to perform normalization or correction of the phantom size values. The user may input his choice through the graphical user interface by clicking or pressing a designated button on the graphical user interface so as to trigger an action to normalize the phantom size values. In an embodiment, the graphical user interface may contain an option to save the choice made by the user, to be applied as a default for all the future medical studies. For example, normalization of phantom size values may be performed as a default action if a mismatch is identified between the age of the patient and the phantom size value. If the user chooses to perform normalization/correction of the phantom size values, the processing unit 201 performs normalization of the phantom size at act 806 and corrects the dose values in the medical study at act 807, according to the normalized phantom size. At act 808, a structured report including the correct dose values corresponding to the normalized phantom size is generated.

Figure 9:
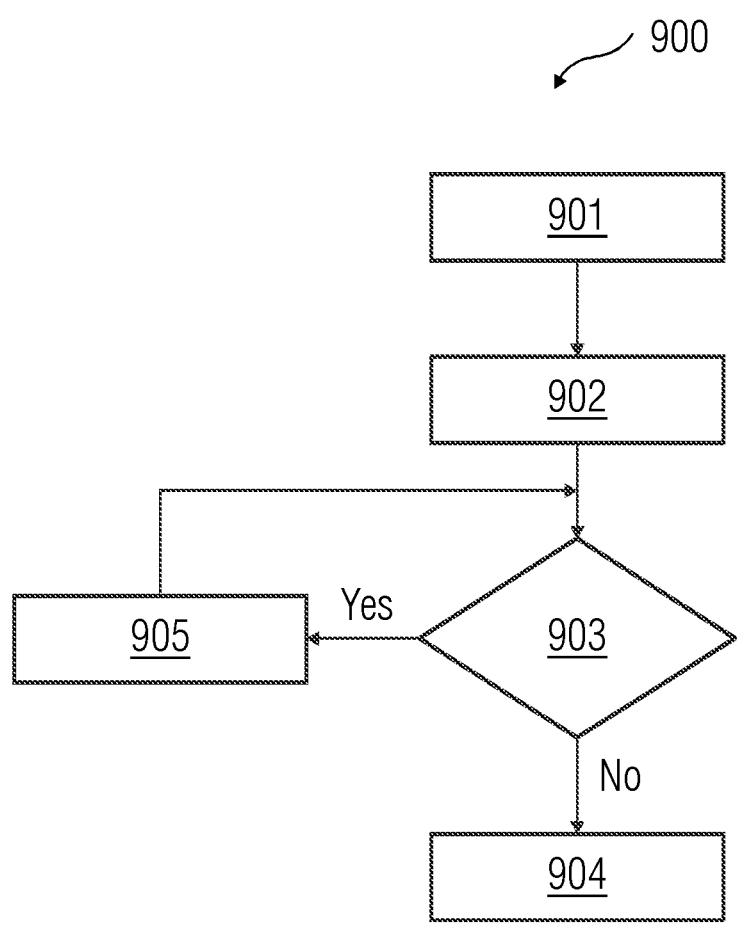
FIG. 9 illustrates a flowchart of an additional embodiment of a method of correcting a parameter in a medical study.

FIG. 9 provides an illustration of a flowchart of an embodiment of a method 900 for correcting a parameter in a medical study. In the embodiment, the parameter to be validated in the medical study is a DICOM tag. A DICOM tag enables identification of an attribute in a medical study. At act 901 of the method 900, a DICOM tag value to be validated is determined from the medical study/DICOM study by the processing unit 201. At act 902, a corresponding DICOM tag value in the imaging protocol is determined by the processing unit 201. The DICOM tag values from the DICOM study and imaging protocol are compared to identify if there is a mismatch, at act 903 of the method 900. If there is a mismatch, the tag value in the DICOM study is corrected based on the tag value presented in the imaging protocol, at act 905. A structured medical report is generated at act 904 with correct DICOM tag values such that the medical report is valid.

Figure 10:
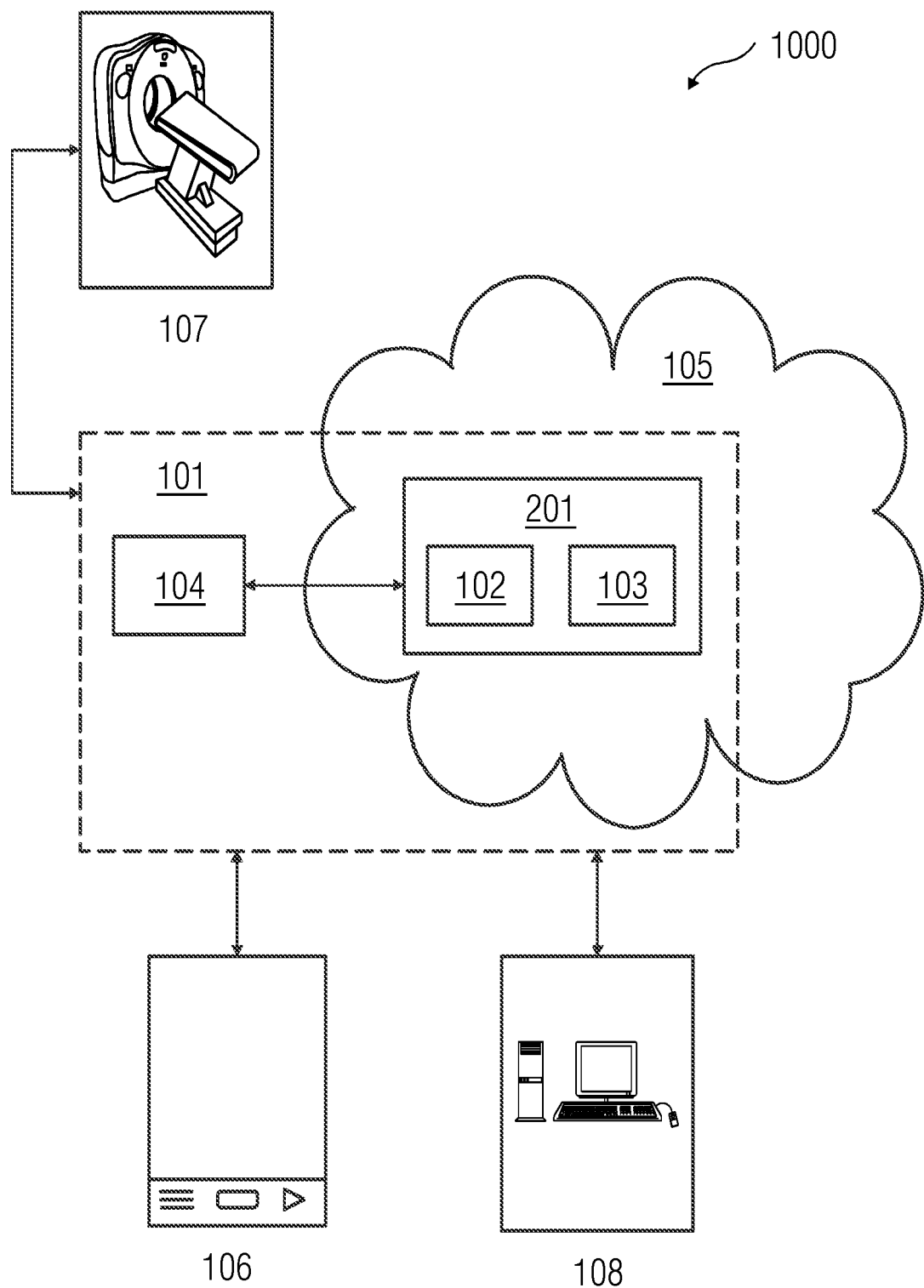
FIG. 10 illustrates a block diagram of another client-server architecture that provides geometric modeling of components representing different parts of a real world object, according to an embodiment.

FIG. 10 provides an illustration of another client-server architecture that provides a geometric modeling of components of a system 1000 for validation of a parameter in a medical study. The system 1000 includes a medical scanner 107 coupled to a local transmission unit 101. The local transmission unit includes an interface 104, a medical database 102, and a validation module 103 in a cloud computing environment 105. The medical scanner communicates with the cloud computing environment 105 through the interface 104 of the local transmission unit 101. In an embodiment, the medical scanner 107 includes a cloud adapter module that connects the medical scanner 107 with the cloud computing environment 105. Therefore, the medical study received/generated by the medical scanner is transferred to the cloud computing environment 105 through the cloud adapter module. The medical study is stored in the medical database 102. The cloud computing environment 105 includes components of the local transmission unit 101 such as the validation module 103. The validation module 103 is configured to validate a parameter in the medical study. In an embodiment, the cloud computing environment 105 includes an additional component of the local transmission unit 101 such as the notification module. The notification module is configured to generate an alert or notification on a user device (e.g., a mobile device 106 or a computing unit 108 of the user) to notify the user of the mismatch in the parameter in the medical study. The validation module 103 is further configured to receive a choice from the user through the graphical user interface of the mobile device 106 or the computing unit 108 for performing normalization and correction of the parameter in the medical study. Therefore, validation of the parameter in the medical study is performed in the cloud computing environment 105. The cloud computing environment 105 enables the medical study to be accessed by more than one user at the same time. The cloud computing environment 105 also provides a secure environment for performance of validation of the parameter and storing the corrected medical study.

The foregoing examples have been provided merely for the purpose of explanation and are in no way to be construed as limiting the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method of validating a parameter in a medical study, the method comprising:
   receiving, by an interface, the medical study from a source;
   determining, by a processor, a first parameter of the medical study to be validated;
   receiving an imaging protocol from a configuration file in an imaging unit by the interface, wherein the imaging protocol comprises a second parameter corresponding to the first parameter in the medical study;
   determining, by the processor, if there is a mismatch of the first parameter in the medical study and the second parameter in the imaging protocol; and
   generating a validated medical study when there is a mismatch, wherein generating the validated medical study comprises:
   in response to the mismatch, normalizing, by the processor, a phantom size in the imaging protocol based on an age of a patient; and
   correcting, by the processor, the first parameter in the medical study based on the normalized phantom size in the imaging protocol.

2. The method of claim 1, wherein the medical study is a digital imaging and communications in medicine (DICOM) study.

3. The method of claim 1, wherein determining if there is a mismatch of the first parameter and the second parameter comprises comparing, by the processor, the first parameter in the medical study with the corresponding second parameter in the imaging protocol.

4. The method of claim 1, wherein correcting the first parameter in the medical study comprises determining, by the processor, the age of the patient being examined, the phantom size, or the age of the patient being examined and the phantom size.

5. The method of claim 1, wherein correcting the first parameter in the medical study comprises:
   comparing, by the processor, the second parameter in the imaging protocol with the first parameter in the medical study; and
   when there is a mismatch:
      determining, by the processor, a dose index value in the imaging protocol;
      determining, by the processor, a scan length value in the imaging protocol;
      determining, by the processor, the second parameter, the determining of the second parameter comprising calculating a product of the dose index value and the scan length value; and
      correcting, by the processor, the first parameter in the medical study based on the determined second parameter.

6. The method of claim 5, wherein the first parameter is a dose length product value in the medical study, and the second parameter is a dose length product value in the imaging protocol.

7. The method of claim 1, wherein the first parameter of the medical study comprises dose values accumulated after an irradiation event of medical imaging.

8. The method of claim 1, wherein the first parameter of the medical study comprises a DICOM tag.

9. The method of claim 1, wherein the second parameter of the imaging protocol comprises dose values defined for an irradiation event of medical imaging.

10. The method of claim 4, further comprising:
    applying, by the processor, normalization of the phantom size as a default action when there is a mismatch between the age of the patient being examined and the phantom size.

11. A local transmission unit for validating a parameter in a medical study, the local transmission unit comprising:
    an interface configured to:
       receive the medical study from a source, wherein the medical study comprises a first parameter; and
       receive an imaging protocol from a configuration file in an imaging unit, wherein the imaging protocol comprises a second parameter corresponding to the first parameter in the medical study; and a processor configured to:
   determine the first parameter of the medical study to be validated;
   determine if there is a mismatch of the first parameter in the medical study and the second parameter in the imaging protocol; and
   generate a validated medical study when there is a mismatch, wherein generation of the validated medical study comprises:
      in response to the mismatch, normalization of a phantom size in the imaging protocol based on an age of a patient; and
      correction of the first parameter in the medical study based on the normalized phantom size in the imaging protocol.

12. The local transmission unit of claim 11, wherein the determination of if there is a mismatch of the first parameter and the second parameter comprises comparison of the first parameter in the medical study with the corresponding second parameter in the imaging protocol.

13. The local transmission unit of claim 11, wherein the correction of the first parameter in the medical study comprises determination of the age of the patient being examined, the phantom size, or the age of the patient being examined and the phantom size.

14. The local transmission unit of claim 11, wherein correction of the first parameter in the medical study comprises:
   comparison of the second parameter in the imaging protocol with the first parameter in the medical study; and
   when there is a mismatch:
   determination of a dose index value in the imaging protocol;
   determination of a scan length value in the imaging protocol;
   determination of the second parameter, the determination of the second parameter comprising calculation of a product of the dose index value and the scan length value; and
   correction of the first parameter in the medical study based on the determined second parameter.

15. A system for validating a parameter in a medical study, the system comprising:
   a medical scanner configured to scan an object and generate a medical study, wherein the medical study comprises a first parameter;
   a local transmission unit comprising:
      an interface configured to receive the medical study from the medical scanner; and
   a processor in a cloud computing environment, wherein the processor is configured to:
      determine the first parameter of the medical study to be validated;
      determine if there is a mismatch of the first parameter in the medical study and the second parameter in the imaging protocol; and
      generate a validated medical study when there is a mismatch, wherein the generation of the validated medical study comprises:
         in response to the mismatch, normalization, by the processor, of a phantom size in the imaging protocol based on an age of a patient; and
         correction, by the processor, of the first parameter in the medical study based on the normalized phantom size in the imaging protocol.

16. A non-transitory computer-readable storage medium that stores machine-readable instructions executable by a server to validate a parameter in a medical study, the instructions comprising:
   receiving, by an interface, the medical study from a source;
   determining, by a processor, a first parameter of the medical study to be validated;
   receiving, by the interface, an imaging protocol from a configuration file in an imaging unit, wherein the imaging protocol comprises a second parameter corresponding to the first parameter in the medical study;
   determining by the processing unit if there is a mismatch of the first parameter in the medical study and the second parameter in the imaging protocol; and
   generating a validated medical study when there is a mismatch, wherein generating the validated medical study comprises:
      in response to the mismatch, normalizing, by the processor, a phantom size in the imaging protocol based on an age of a patient; and
      correcting, by the processor, the first parameter in the medical study based on the normalized phantom size in the imaging protocol.

17. The non-transitory computer-readable storage medium of claim 16, wherein determining if there is a mismatch of the first parameter and the second parameter comprises comparing, by the processor, the first parameter in the medical study with the corresponding second parameter in the imaging protocol.

18. The non-transitory computer-readable storage medium of claim 16, wherein correcting the first parameter in the medical study comprises determining the age of the patient being examined, a phantom size or the age of the patient being examined and the phantom size.

19. The non-transitory computer-readable storage medium of claim 16, wherein correcting the first parameter in the medical study comprises:
   comparing, by the processor, a second parameter in the imaging protocol with the first parameter in the medical study; and
   when there is a mismatch:
   determining, by the processor, a dose index value in the imaging protocol;
   determining, by the processor, a scan length value in the imaging protocol;
   determining, by the processor, the second parameter, determining the second parameter comprising calculating a product of the dose index value and the scan length value; and
   correcting, by the processor, the first parameter in the medical study based on the determined second parameter.

* * * * *